United States Patent [19]

Chung et al.

[11] Patent Number: 5,561,050

[45] Date of Patent: Oct. 1, 1996

[54] METHODS FOR DIAGNOSIS OF COLON, STOMACH AND PANCREATIC CANCER USING ANTIBODIES SPECIFIC FOR A MUCIN-TYPE CARBOHYDRATE CHAIN

[75] Inventors: Yong-Suk Chung; Yoshito Yamashita; Michio Sowa, all of Osaka; Ryuichi Horie, Kawasaki; Takashi Saito, Kanagawa-ken; Keiichi Murayama, Ebina, all of Japan

[73] Assignee: Tosoh Corporation, Shinnanyo, Japan

[21] Appl. No.: 432,005

[22] Filed: May 1, 1995

Related U.S. Application Data

[63] Continuation of Ser. No. 162,911, Dec. 8, 1993, abandoned.

[30] Foreign Application Priority Data

Dec. 9, 1992 [JP] Japan ................................. 4-329414

[51] Int. Cl.$^6$ ........................... G01N 33/53; C07K 16/30; C12N 5/20
[52] U.S. Cl. .................... 435/7.23; 435/240.27; 435/7.92; 530/387.3; 530/387.5; 530/387.7; 530/388.8
[58] Field of Search .................. 435/7.23, 7.92, 435/240.27; 530/387.5, 387.7, 388.8, 397

[56] References Cited

U.S. PATENT DOCUMENTS 4,444,744  4/1984  Goldenberg .

FOREIGN PATENT DOCUMENTS 3280894  12/1991  Japan .

OTHER PUBLICATIONS

Waldmann, Science 252:1657–1602, 1991.
Harris et al. Tibtech 11:42–44, 1993.
Ho et al., Int. J Cancer 52:693–700, 11 Nov. 1992.
Yamashina et al. GANN 29:149–56, 1983.
Yamashita et al. Proc. Am. Assoc. Cancer Res 34: Mar. 1993.
Stites et al. "Basic & Clinical Immunology", Appleton & Lange, 1987, pp. 241–303.
K. L. Matta et al., "Synthetic Antigen as Immunogen", Immunological Investigations, vol. 20, No. 5–6, 1991, pp. 525–537.
D. J. Handley et al., "Antigenic Studies on an Enzymatically Sialylated Carbohydrate:", Immunological Investigations, vol. 20, No. 1, Feb. 1991, pp. 21–32.
Patent Abstract of Japan, vol. 00, No. 9241, JP–A–60 098 000, Sep. 1985.

*Primary Examiner*—Paula K. Hutzell
*Attorney, Agent, or Firm*—Foley & Lardner

[57] ABSTRACT

Methods for diagnosis of cancers of digestive organs selected from stomach, colon and pancreatic cancers using antibodies specific for a mucin-type carbohydrate chain of the formula Gal$\beta$1—4GlcNAc$\beta$1—6GalNAc$\alpha$1—1Cer are described.

12 Claims, No Drawings

METHODS FOR DIAGNOSIS OF COLON, STOMACH AND PANCREATIC CANCER USING ANTIBODIES SPECIFIC FOR A MUCIN-TYPE CARBOHYDRATE CHAIN

This application is a continuation of application Ser. No. 08/162,911, filed Dec. 8, 1993, now abandoned.

The present invention relates to a cancer-related pharmaceutical composition containing an antibody capable of recognizing a carbohydrate chain.

It has been reported that when a cell is cancerated, a carbohydrate chain which is not observed in a normal cell, can be detected on the surface of the cancer cell.

On the other hand, among antibodies prepared for the practical purpose of obtaining antibodies useful for diagnosis or therapy of cancer, there are many antibodies which are capable of recognizing abnormal carbohydrate chains of cancer cells, and some of them are presently used for serodiagnosis of cancer. However, most of such antibodies are obtained by a method wherein a mouse is immunized with human cancer cells, and they are not necessarily designed for particular specific carbohydrate chains as their targets.

Thus, a methodology has been popular in recent years in which a carbohydrate chain antigen of cancer is to be used as a so-called tumor marker for diagnosis or therapy. However, no tumor marker having adequate sensitivity and specificity has been developed yet.

Among various carbohydrate chain antigens, the present inventors have paid a particular attention to carbohydrate chains of glycoproteins, particularly to mucin-type carbohydrate chains. It is known that they not only are present in the surface layer of cells but also will be secreted. Further, their cancerous change has been reported. Namely, if it is possible to obtain an antibody to a mucin-type carbohydrate chain which is specific to a cancer, such an antibody is expected to be capable of specifically recognize the cancer-related antigen. However, when a monoclonal antibody is prepared using a glycoprotein as the antigen, an antibody to the protein moiety will be obtained, whereby it is difficult to obtain an antibody to the specific mucin-type carbohydrate chain.

Thus, it was difficult to have a cancer-related antigen specifically recognized by an antibody capable of recognizing a mucin-type carbohydrate chain of glycoprotein. Therefore, the present inventors prepared an antibody which is capable of recognizing a synthetic glycolipid derivative having a mucin-type carbohydrate chain of glycoprotein and ceramide bonded to each other, and confirmed that such an antibody reacted specifically with the glycolipid derivative (see Japanese Unexamined Patent Publication No. 280894/1991).

However, it was not known if such an antibody was capable of specifically recognizing a cancer, and no study was made as to whether or not such an antibody was useful for diagnosis or therapy of a cancer.

The present inventors have conducted extensive studies on the reactivity of antibodies and cancer tissues and as a result, have found that an antibody capable of recognizing a certain type of mucin-type carbohydrate chain, is capable of specifically recognizing cancer tissues. The present invention has been accomplished on the basis of this discovery.

Thus, the present invention provides a cancer-related pharmaceutical composition containing, as an active ingredient, an antibody capable of recognizing a mucin-type carbohydrate chain of the formula (1):

(1).

Now, the present invention will be described in detail with reference to the preferred embodiments.

For the purpose of the present invention, the pharmaceutical composition includes, for example, a diagnostic agent and a therapeutic agent for cancer. As such a diagnostic agent for cancer, it can be applied to various methods employing antibodies. For example, an enzymelinked immunosorbent assay (ELISA) by a sandwich EIA method or a competition method, a radioimmunoassay (RIA), or a method employing a site fluorometric analysis (FACS) may be mentioned.

The type of diagnosis may, for example, be detection of a cancer-related antigen in a body fluid such as blood or urine (such as serodiagnosis), detection of a cancer-related antigen in a tissue or in a cell (such as histological diagnosis or cytodiagnosis), or a method wherein an antibody labelled with a radioactive isotope is administered in a body to detect a tumor.

The therapeutic agent for cancer may likewise be applied to various methods employing antibodies. For example, a method may be mentioned wherein the antibody is administered into a body by itself or in the form of a therapeutic agent having the antibody bonded to a substance showing cytotoxicity such as a toxin or radioactive isotope.

The antibody to be used in the present invention is an antibody which is capable of recognizing a carbohydrate chain of the formula (1). For example, it may be monoclonal antibody Flα-75, Flα-50 or Flα-87 as disclosed in Japanese Unexamined Patent Publication No. 280894/1991, which is capable of recognizing a glycolipid of the formula (2).

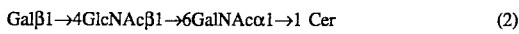

(2)

The antibody of the present invention may be prepared by a conventional method or a method of using genetic engineering. The conventional method differs as between a monoclonal antibody and a polyclonal antibody.

A monoclonal antibody can be produced in accordance with a method of G. Köhler et al, Nature, 256, 495–497 (1975), which comprises immunizing an animal with an antigen, taking out spleen cells, hybridizing the spleen cells with myeloma cells, and culturing the hybridoma cells thereby obtained.

For example, as a method of obtaining a hybridoma which produces the antibody to be used in the present invention, a method disclosed in Japanese Unexamined Patent Publication No. 280894/1991, may be mentioned. The obtained hybridoma may be cultured in the same manner as a usual hybridoma, whereby the antibody will be produced in the culture medium. Otherwise, the hybridoma may be transplanted to e.g. a mouse, whereby the monoclonal antibody may be produced in the ascites.

A polyclonal antibody may also be obtained by a conventional method which comprises immunizing an animal with a glycolipid of the formula (2) and obtaining the antiserum.

In the method of using gene engineering, a mouse is immunized with a glycolipid of the formula (2), then spleen cells are taken out, RNA is extracted, and a cDNA library is prepared, and the desired gene is isolated using the reactivity with the antibody as an index. Then, microorganisms or animal cells having the antibody expression vector introduced, are cultured to produce the antibody, which is then purified by a usual method.

Thus, the antibody to be used in the present invention may not necessarily be an antibody of natural type and may be an artificial antibody prepared by means of a gene engineering method or a protein chemical method. As an example of the artificial antibody prepared by means of a gene engineering method, a chimera antibody may be mentioned which has a structure wherein the variable region necessary for bonding with an antigen is derived from a mouse and the constant region which is unnecessary for bonding with an antigen is derived from a human being, may be mentioned.

Such a method for the preparation of the antibody may be conducted by a method which is per se well known in the art.

On the other hand, as an example of the artificial antibody prepared by means of a protein chemical method, a fragmented antibody such as Fab prepared by digesting an antibody molecule with an enzyme such as papain or pepsin, may be mentioned. Otherwise, it may be prepared as a part of a so-called Bispecific antibody bonded with an antibody capable of recognizing antitumor cells such as NK cells or LAK cells.

The antibody capable of recognizing a carbohydrate chain of the formula (1) to be used in the present invention, may be used as a cancer-related pharmaceutical, particularly as a pharmaceutical composition against a cancer of a digestive organ. Especially, it shows a very high positive reaction to a cancer of the stomach, and it is particularly useful as a pharmaceutical composition against a stomach cancer. Now, the present invention will be described in further detail with reference to Examples. However, it should be understood that the present invention is by no means restricted to such specific Examples.

In these Examples, monoclonal antibody Flα-75 obtained by immunization with a glycolipid of the formula (2) in accordance with the method as disclosed in Japanese Unexamined Patent Publication No. 280894/1991, was used.

EXAMPLE 1

Recognition of stomach cancer tissues by monoclonal antibody capable of recognizing glycolipid The reactivity of monoclonal antibody Flα-75 against stomach cancer tissues was examined by applying a technique of immunological tissue staining to stomach cancer tissue sections. As the cancer tissues, cancer tissue sections taken out from patients of stomach cancer were used as test samples. The immunological tissue staining test using the antibody, was conducted as follows.

Namely, a tissues sample was fixed with 10% formalin and then embedded in paraffin. The paraffin block was sectioned to obtain thin sections of 3 μm. The sections were subjected to paraffin removal treatment and then treated with a 0.3% hydrogen peroxide methanol solution to remove intrinsic peroxidase. A sample containing an antibody to be tested, was reacted therewith at room temperature for one hour. Then, the sections were treated in accordance with the procedure of an enzyme antibody method employing ABC kit manufactured by Lipshaw/Immunon Co., and hematoxylin was used for counter staining.

The stainability of tissues was evaluated by the following evaluation standards:

(−): Cancer tissues were not stained at all.

(+): The stained area was less than 5%.

(++): The stained area was from 5 to 30%.

(+++): The stained area was more than 30%.

81 Cases of stomach cancer were examined, and the results were as follows.

The normal stomach tissues were not stained, and with respect to the stomach cancer tissues, 21.0% was (−), 29.6% was (+), 29.6% was (++) and 19.8% was (+++), and the overall positive rate was 79.0%. Further, 27.0% of the mucoepithelium adjacent to the cancer was stained, which indicates that such tissues were close to a cancerous state.

From the study based on the types of tissues of stomach cancer, it was found that the low differential adeno carcinoma showed the highest positive rate of 92.1%, the moderately differential tubular adeno carcinoma showed a positive rate of 76.5%, the papillary adeno carcinoma showed a positive rate of 63.6%, and the highly differential tubular adeno carcinoma showed a positive rate of 57.1%.

The positive rate in the stomach cancer at an early stage was 58.3%, and the positive rate in the progressive stomach cancer was 79.2%.

Thus, monoclonal antibody Flα-75 exhibited a high positive rate to the stomach cancer irrespective of the tissues type or the degree of the progress, while it did not react with normal stomach tissues.

EXAMPLE 2

Recognition of colon cancer tissues by monoclonal antibody Flα-75

The reactivity of monoclonal antibody Flα-75 against colon cancer tissues was examined by applying a technique of immunological tissue staining to colon cancer tissue sections. As the cancer tissues, cancer tissue sections taken out from patients of colon cancer were used as test samples. The immunological tissue staining test using the antibody, was carried out in the same manner as in Example 1.

78 Cases of colon cancer were examined, and the results were as follows. (The evaluation standards used were the same as in Example 1.)

The normal colic tissues were not stained, and with respect to colon cancer tissues, 61.6% was (−), 20.5% was (+), 16.4% was (++) and 1.4% was (+++), and the overall positive rate was 38.4%.

From the study based on the types of tissues of colon cancer, the highly differential adeno carcinoma showed a positive rate of 43.5%, and the moderately differential adeno carcinoma showed a positive rate of 30.0%.

Thus, monoclonal antibody Flα-75 exhibited a high reactivity to the colon cancer, while it did not react with normal colon tissues.

EXAMPLE 3

Recognition of pancreatic cancer tissues by monoclonal antibody Flα-75

The reactivity of monoclonal antibody Flα-75 against pancreatic cancer tissues was examined by applying a technique of immunological tissue staining to pancreatic cancer tissue sections. As the cancer tissues, cancer tissue sections taken out from patients of pancreatic cancer were used as test samples. The immunological tissue staining test using the antibody, was carried out in the same manner as in Example 1.

As a result, a staining reaction specific to cancer tissues was observed with respect to tissue sections of four cases among seven cases of pancreatic cancer. the positive rate was 57.1%.

It is evident from the above results that the antibody capable of recognizing a mucin-type carbohydrate chain of the formula (1), is able to specifically recognize cancer tissues. Thus, such an antibody is useful as a diagnostic agent or a therapeutic agent for cancer.

Thus, the pharmaceutical composition containing the antibody capable of recognizing a mucin-type carbohydrate chain of the formula (1) presents a useful means for diagnosis or therapy of cancer.

What is claimed is:

1. A method for diagnosing a cancer of a digestive organ selected from the group consisting of the stomach, the colon and the pancreas, comprising the steps of contacting an antibody capable of recognizing a mucin-type carbohydrate chain of the formula (2):

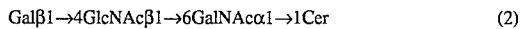 (2)

with a body fluid or with tissue or a cell of the respective digestive organ and detecting whether said antibody has bound to an antigen.

2. The method according to claim 1, wherein said method is an enzyme-linked immunosorbent assay.

3. The method according to claim 1, wherein said method is a sandwich EIA method.

4. The method according to claim 1, wherein said method is a competition assay.

5. The method according to claim 1, wherein said method is a radioimmunoassay.

6. The method according to claim 1, wherein said method is a site fluorometric analysis assay.

7. The method according to claim 1, wherein the antibody is contacted with a blood sample.

8. The method according to claim 1, wherein the antibody is contacted with a urine sample.

9. The method according to claim 1, wherein the antibody is contacted with a tissue sample from the respective organ.

10. The method according to claim 1, wherein the antibody is labeled with a radioactive isotope and administered to a subject to detect said cancer.

11. The method according to claim 1, wherein the antibody is a rodent monoclonal antibody, a polyclonal antibody or a chimera antibody having a variable region from a mouse and a human constant region.

12. The method according to claim 1, wherein the antibody is contacted with a tissue sample from the respective organ or a blood sample.

* * * * *